United States Patent [19]

Matolcsy et al.

[11] Patent Number: 5,055,125

[45] Date of Patent: Oct. 8, 1991

[54] ANTIDOTED HERBICIDE COMPOSITIONS AND ANTIDOTE COMPOSITIONS

[75] Inventors: György Matolcsy; Antal Gimesi; Antalné Tombor; Barna Bordás, all of Budapest; Jánosné Benczik; Zoltán Kolonics, both of Balatonalmádi; Csaba Söptei, Veszprém; Sándor Boros, Balatonalmádi; Ágota Kéner, Füzfogyártelep; Denzso Sebok; Géza Szabó, both of Veszprém; Imre Varga, Balatonalmádi, all of Hungary

[73] Assignee: Nitrokémia Ipartelepek, Budapest, Hungary

[21] Appl. No.: 507,314

[22] Filed: Apr. 10, 1990

[30] Foreign Application Priority Data

Apr. 11, 1989 [HU] Hungary ............ 2251-1720/89

[51] Int. Cl.$^5$ ............................................ A01N 43/76
[52] U.S. Cl. .................................. 71/88; 71/98; 71/100; 71/101; 71/118; 548/216
[58] Field of Search ............ 548/216; 71/100, 101, 71/88, 118, 98

[56] References Cited

U.S. PATENT DOCUMENTS

| 3,134,666 | 5/1964 | McRae | 71/100 |
|---|---|---|---|
| 3,442,945 | 5/1969 | Olin | 71/88 |
| 3,547,620 | 12/1970 | Olin | 71/88 |
| 4,021,224 | 5/1977 | Pallos et al. | 71/100 |
| 4,231,786 | 11/1980 | Czajkowski et al. | 71/101 |

FOREIGN PATENT DOCUMENTS 2043447 10/1980 United Kingdom ............ 71/88

Primary Examiner—Allen J. Robinson
Assistant Examiner—John D. Pak
Attorney, Agent, or Firm—Schweitzer Cornman & Gross

[57] ABSTRACT

Herbicidal compositions comprising a substituted thiolcarbamate derivative corresponding to the formula (I) wherein $R_1$, $R_2$ and $R_3$ are selected independently from alkyl groups having 1 to 4 carbon atoms and/or a chloroacetanilide derivative corresponding to the formula (II) wherein $R_4$ and $R_5$ are hydrogen or alkyl group having 1 to 4 carbon atoms, identical or different, $R_6$ is an alkoxyalkyl group corresponding to the formula $—R_7—O—R_8$ in which $R_7$ and $R_8$ are selected from alkyl groups having 1 to 4 carbon atoms and, as an antidote, a thiocarbamic acid derivative corresponding to the formula (III) wherein $R_9$ and $R_{10}$ independently from each other are alkyl or alkenyl group having 1 to 4 carbon atoms, or $R_9$ and $R_{10}$ taken together with one or two nitrogen atoms form a heterocyclic group, which may contain one oxygen atom or they form a soiro-heterocyclic or condensated ring, which can be substituted with alkyl groups having 1 to 4 carbon atoms or an aryl group, $R_{11}$ is an alkyl or alkenyl group having 1 to 3 carbon atoms or a benzyl group containing one or 2 substituents, carboxy methylene, 1-methylene naphtyl, acetophenon-(2)-yl-, carb-($\alpha$)naphthoxymethylene, N-methylene o-benzoic acid sulphimide, N-isopropyl-N-phenylacetamidyl, N,N-disubstituted-2-acetamidyl group containing alkyl, alkylene groups having 1 to 3 carbon atoms, alkoxyalkyl, phenyl or dialkyl phenyl group.

7 Claims, No Drawings

ANTIDOTED HERBICIDE COMPOSITIONS AND ANTIDOTE COMPOSITIONS

This invention relates to selective herbicide compositions containing a substituted thiolcarbamate derivative and/or a chloroacetanilide derivative as herbicidal agents and a dithiocarbamic acid derivative as antidote as well as to antidote compositions containing a dithiocarbamic acid derivative as active ingredient.

One of the most important requirements to herbicide compositions is their selectivity, i.e. it is efficient in weed control among cultivated plants while ineffective on the growth of the crop. Several known herbicidal agents, however, are detrimental more or less to the cultivated plant even though they are excellent weed-killers like thiolcarbamate derivatives.

Some examples of thiolcarbamate derivative-based herbicide preparations are claimed in the U.S. Pat. Nos. 2,913,327 and 3,175,897. Thus, one of the well-proved agents is S-ethyl-N,N-dipropylthiocarbamic ester (EPTC).

Such compositions are excellent in weed control but may impair the crop to be controlled, e.g. maize.

Another family of well-known outstanding herbicidal agents is chloroacetanilide derivatives. Their weed-killing activity is described e.g. in the U.S. Pat. Nos. 3,442,945 and 3,547,620. The best known members of the family are:

2-chloro-N-(ethoxymethyl)-N-(2-ethyl-6-methyl-phenyl)acetamide (acetochlor) and
2-chloro-N-(2,6-diethylphenyl)-N-(methoxymethyl)-acetamide (alachlor).

Compositions thereof have outstanding herbicidal effect but may be detrimental to the cultivated plants, e.g. maize.

As a practical realization of selective weed control, an antidote, i.e. an antagonistic agent to the impairment of the cultivated plant, is admixed to the herbicidally active ingredient or to the herbicidal composition. In an alternative realization, the herbicide composition is applied together with the antidote composition. In these cases, the crop remains unharmed without any loss in the weed-killing efficiency.

Antidotes against the detrimental effect of thiolcarbamate-based herbicide compositions to the cultivated plants, especially to maize, are described e.g. the Belgian Pat. Nos. 782,120 and 806,038, in the U.S. Pat. Nos. 3,893,838 and 3,931,313, in the Brit. Pat. Nos. 1,420,685 and 1,512,540 as well as in the Hungarian Pat. Nos. 165,736, 168,977; 173,775, 174,487 and 187,284.

In the agricultural practice, the well-known antidote, N,N-diallyl-dichloroacetamide (R-25788) has been extended (as claimed in the Hungarian Pat. No. 165,736).

Antidotes against the detrimental effect of chloroacetanilide-based herbicide compositions to the cultivated plants, especially to maize, are described in the Eur. Pat. No. 054,278 and in the Hungarian Pat. No. 187,284.

In spite of the considerable results in the research of antidotes, selectivity, efficiency and effective range of antidote-containing compositions want to be enhanced and the assortment should be extended by even more effective antidoted preparations.

It has been discovered in this research that compositions containing some kinds of dithiocarbamate derivatives are outstanding antidotes for herbicidal agents and herbicide compositions, mainly those containing thiolcarbamate derivatives and/or chloroacetanilides, i.e. they are antagonists (reduce or even eliminate) in any influence on growth of the cultivated plants without any suppressing in the efficiency of weed control.

Accordingly, this invention comprises compositions containing as herbicidal agents thiolcarbamate derivatives corresponding to the formula

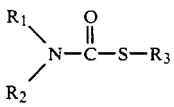

(I) wherein, $R_1$, $R_2$, and $R_3$ are selected independently from alkyl groups having 1 to 4 carbon atoms, $R_1$ or $R_2$ may be a cycloalkyl group having 4 to 6 carbon atoms, or $R_1$ and $R_2$ together form a 5 to 7 membered saturated ring; and/or chloroacetanilides corresponding to the formula

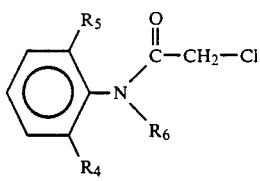

(II) wherein $R_4$ and $R_5$ are hydrogen or alkyl group having 1 to 4 carbon atoms, identical or different, $R_6$ is an alkoxyalkyl group having the formula $-R_7-O-R_8$ in which $R_7$ and $R_8$ are selected from alkyl groups having 1 to 4 carbon atoms.

Supplementing thiolcarbamate and/or chloroacetanilide herbicides by a dithiocarbamate derivative of the formula

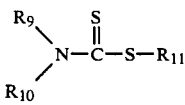

(III) as a safener, the safening (protecting) effect of the composition is superior to that with a composition containing a known safener (antidote). In the compounds of the formula (III) the substituents represent the following groups:

$R_9$ and $R_{10}$ independently from each other are alkyl or alkenyl group having 1 to 4 carbon atoms, or $R_9$ and $R_{10}$ taken together with one or two nitrogen atoms form a heterocyclic group, which may contain one oxygen atom or they form a spiro-heterocyclic or condensed ring, which can be substituted with alkyl groups having 1 to 4 carbon atoms or an aryl group, $R_{11}$ is an alkyl or alkenyl group having 1 to 3 carbon atoms or a benzyl group containing one or 2 substituents, carbethoxy methylene, 1-methylene naphthyl, acetophenon-(2)-yl-, carb-(α)naphthoxy-methylene, N-methylene o-benzoic acid sulphimide, N-isopropyl-N-phenyl-acetamidyl, N,N-di-substituted-2-acetamidyl group containing alkyl, alkylene groups having 1 to 3 carbon atoms, alkoxyalkyl, phenyl or dialkyl phenyl group.

Application of compositions of this invention is beneficial to those used currently as they are more selective and provide better protection to the crop against the detrimental effect of the herbicide.

The most preferred thiolcarbamates in this invention are: N,N-di(n-propyl)-S-ethylthiocarbamate, N,N-di(n-propyl)-S-n-propylthiolcarbamate, N,N-di(i-butyl)-S-ethylthiocarbamate, N,N-hexamethylene-S-ethylthiolcarbamate, N-cyclohexyl-N-ethyl-S-ethylthiolcarbamate, N-butyl-N-ethyl-S-propylthiocarbamate.

The most preferred chloroacetanilides in this invention are: 2-chloro-N-ethoxymethyl-N-(2'-ethylphenyl-)acetamide (acetochlor) and 2-chloro-N-(2',6'-diethylphenyl)-N-methoxymethyl-acetamide (alachlor).

The most preferred antidotes in this invention are the compounds of the formula

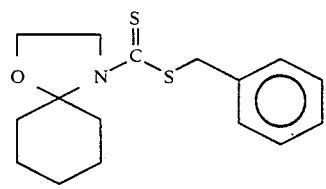 (IV)

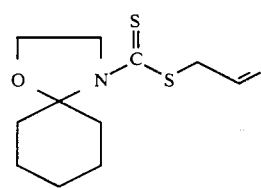 (V)

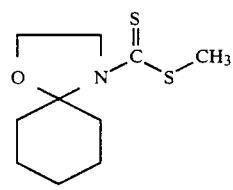 (VI)

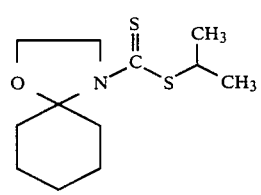 (VII)

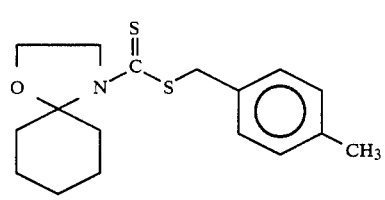 (VIII)

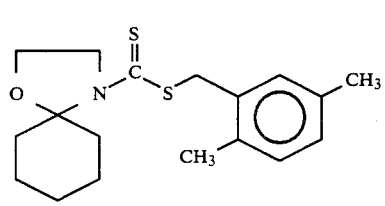 (IX)

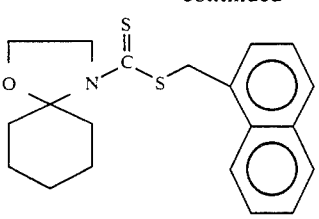 (X)

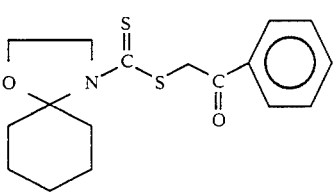 (XI)

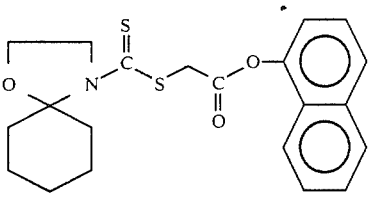 (XII)

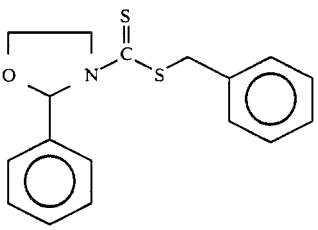 (XIX)

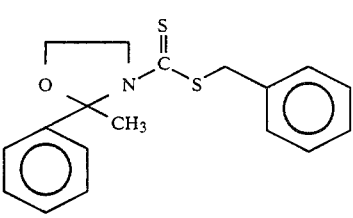 (XX)

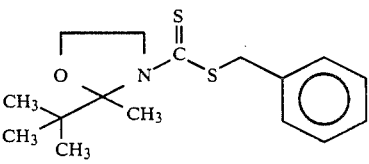 (XXI)

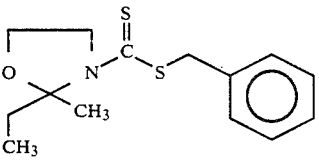 (XXII)

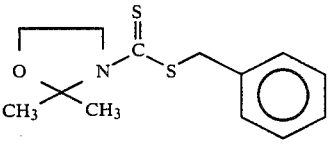 (XXIII)

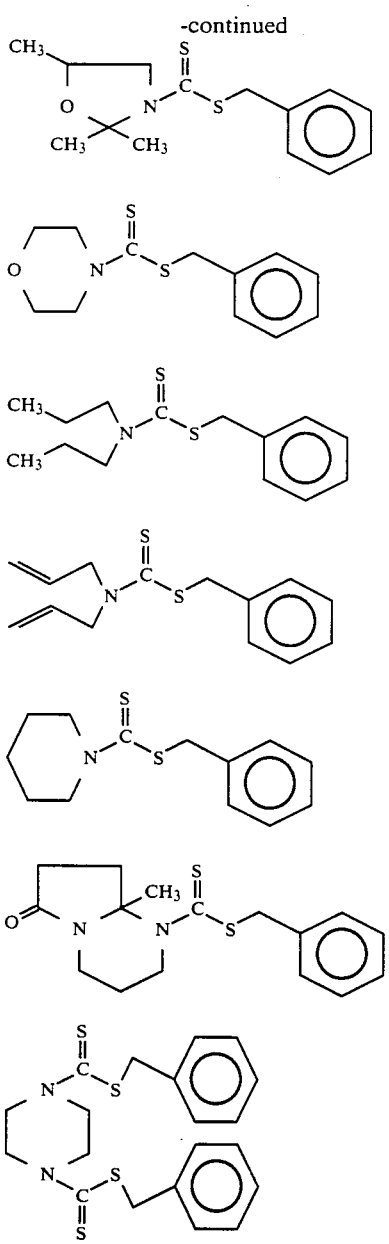

This invention comprises antidoted herbicide compositions containing as active ingredients a substituted thiolcarbamate derivative corresponding to the formula (I) wherein $R_1$, $R_2$, and $R_3$ are selected independently from alkyl groups having 1 to 4 carbon atoms, $R_1$ or $R_2$ may be a cycloalkyl group having 4 to 6 carbon atoms, or $R_1$ and $R_2$ together form a saturated ring having 5 to 7 members; and/or a chloroacetanilide derivative corresponding to the formula (II) wherein $R_4$ and $R_5$ are hydrogen or alkyl group having 1 to 4 carbon atoms, identical or different, $R_6$ is an alkoxyalkyl group having the formula $-R_7-O-R_8$ in which $R_7$ and $R_8$ are selected from alkyl groups having 1 to 4 carbon atoms; and a dithiocarbamic acid derivative corresponding to the formula (III) wherein $R_9$ and $R_{10}$ independently from each other are alkyl or alkenyl group having 1 to 4 carbon atoms, or $R_9$ and $R_{10}$ taken together with one or two nitrogen atoms form a heterocyclic group which may contain one oxygen atom or they form a spiro-heterocyclic or condensed ring, which can be substituted with alkyl groups having 1 to 4 carbon atoms or an aryl group, $R_{11}$ is an alkyl or alkenyl group having 1 to 3 carbon atoms or a benzyl group containing one or 2 substituents, carbethoxy methylene, 1-methylene naphthyl, acetophenon-(2)-yl, carb-($\alpha$)naphtoxy-methylene, N-methylene o-benzoic acid sulphimide, N-isopropyl-N-phenyl-acetamidyl, N,N-disubstitued-2-acetamidyl group containing alkyl, alkylene groups having 1 to 3 carbon atoms, alkoxyalkyl, phenyl or dialkyl phenyl group at a weight ratio herbicide and safener from 50:1 to 5:1. The composition may be supplemented with solid or liquid vehicles and optionally with surfactants; the new compositions have protecting effects superior to those of the known antidoted compositions.

There are also provided by this invention antidote compositions containing from 0.01 to 95 percent by weight, preferably from 0.1 to 90 percent by weight of a dithiocarbamic acid derivative corresponding to the formula (III) wherein $R_9$, $R_{10}$ and $R_{11}$ are substituents as defined above.

The following embodiment of this invention comprises a method of selective weed control in which, prior to or simultaneously with sowing, the soil is treated with a composition containing a thiolcarbamate derivative corresponding to the formula (I) wherein the substituents are as described above, and/or a chloroacetanilide derivative corresponding to the formula (II) wherein the substituents are as described above, and a thiolcarbamic acid derivative corresponding to the formula (III) wherein the substituents are as described above at a rate from 1 to 20 kg/hectare of total active ingredients, or preferably, from 0.05 to 5 kg/hectare of the antidote agent.

Another embodiment of this invention comprises a method of sowing-seed dressing in which sowing-seeds of the cultivated plant to be protected are treated with a dithiocarbamic acid derivative corresponding to the formula (III) wherein the substituents are as described above optionally together with other dressing agents. In the successive application, it is obvious that the herbicidal composition should not procede the protecting agent in order to avoid the deterioration of crop. After protecting, herbicides are applied in any conventional way.

Weight ratio of the active ingredients of a composition containing an antidote, a thiolcarbamate derivative, and/or a chloroacetanilide can be varied within a wide range depending on the chemical structure of the antidote and of the herbicidal agent, on the cultivated plant applied on, and on other factors known by those skilled in the art.

The amount of the antidote applied is adjusted to the per-area need of the herbicidal agent with regard to the weight ratios of this invention. In a joint application, from 1 to 20 kg/hectare of total active ingredients is generally used. In an individual application, the rate of the antidote composition, in term of the active ingredient, may be from 0.05 to 5.0 kg/hectare, preferably from 0.1 to 3.0 kg/hectare, more preferably from 0.5 to 1.0 kg/hectare.

It can be established in general that the compositions containing both herbicide and antidote contain agriculturally acceptable additives compatible with both agents. The term composition refers to either highly concentrated ones or ready-to-use preparations diluted therefrom. In the latter case, the total content of active ingredients may be extremely low, even 0.01 percent by weight. Preparations of herbicidal compositions and antidote compositions blended immediately prior to the application (either in a container or in a sprayer), optionally diluted, are also embodiments of this invention.

The compositions of this invention can be realized as any agriculturally acceptable solid or liquid preparation allowed to prepare and efficiently apply by virtue of the appropriate physical and chemical characteristics of the active ingredient(s). The said preparations contain the active ingredient(s) together with agriculturally acceptable solid or liquid vehicles and surfactant(s).

The preparations may contain other additives that upgrade the efficiency and/or facilitate the application, such as protecting colloids, thickeners, adhesive agents, stabilizers, etc. Other additives extend the period of action (extenders), control other parasites (such as pesticides, fungicides, growth controllers), or act as fertilizers.

Useful vehicles are any agriculturally acceptable, natural or artificial, organic or inorganic, solid or liquid material. Examples of solid vehicles are clay minerals, artificial or natural silicates, silicic acid, dolomite, caolin, diatomaceous earth, ground plant products. Examples of liquid vehicles are water, alcohols, esters, ketones, petroleum fractions, aromatic or aliphatic (cycloaliphatic) hydrocarbons, halogenated hydrocarbons, dimethyl formamide, dimethyl sulfoxide, N-methyl pyrrolidone.

Useful surfactants are ionic and/or non-ionic emulsifiers, dispersants or detergents, such as lignin-sulfonic salts, polycondensates of ethylene oxide with fatty alcohols or fatty acids or fatty acid amides, alkylarylsulfonates, substituted phenols like alkylphenols, arylphenols, and polyoxyethylated phenols. Use of ionic and/or non-ionic surfactants is preferred.

At least one kind of surfactants is necessary in the composition if the active ingredient(s) were insoluble in water and water would be used as diluent.

Liquid compositions of this invention may be solutions, emulsifiable concentrates, emulsions, concentrated suspensions, wettable powders, spray powders or pastes. Concentrated compositions can be diluted to the desired concentrations. Solid preparations of this invention may be powders, dusting powders or granules.

The compositions of this invention can be prepared by any method known by those skilled in the art. The said compositions can be applied, optionally in diluted form, by the conventional procedures and equipment such as by spraying, carburation, dusting, etc. Compounds of the formula (III) are novel used as safeners and can be prepared by methods known in the art.

The following examples illustrate the preparations and biological activity of the compositions of this invention. The Examples serve as illustrations of some embodiments of the invention, however, they do not restrict the scope of invention.

EXAMPLE 1

Preparation of 1,4-oxaza-spiro-(4,5)-decane 120 cm$^3$ of dry benzene, 12.2 g (0.2 mole) of ethanolamine, and 21.6 g (0.22 mole) of cyclohexanone was placed into a round-bottom flask equipped with a Marcuson head. The solution was boiled until the formation of water had ceased. Benzene was distilled off and the residual crude product was used for the following reaction step.

Preparation of 4-(benzyl mercaptothiocarbonyl)-1,4-oxaza-spiro-(4,5)-decane corresponding to the formula (IV)

28.2 g (0.2 mole) of 1,4-oxaza-spiro-(4,5)-decane and 8.0 g (0.2 mole) of sodium hydroxyde dissolved in 80 cm$^3$ of water was placed into a round bottom flask equipped with a reflux condenser, a thermometer, a dropping funnel and a stirrer. Under continuous stirring and cooling 15.2 g (12.05 cm$^3$, 0.2 mole) of carbon disulphide was added dropwise while the temperature was not allowed to rise above 20° C. After the introduction of carbon disulphide the mixture was continued to stir at room temperature for 2 hours. Cooling and continuous stirring was continued and 25.3 g (22.96 ml, 0.2 mole) benzyl chloride was added dropwise below 10° C. Stirring was continued for 2 hours after the introduction had been completed. The aqueous layer was decanted then 20 cm$^3$ of water was added, stirred and decanted three times. The remained rubber-like product was boiled with four-fold amount of hexane. The cooled and filtrated product was a white powder uniform in this layer chromatography.

Yield 28.6 g (46.6%).

Melting point: 154°–155° C.

Elementar analysis: Theoretical: N=4.56, S=20.85. Measured: N=4.51, S=20.86.

EXAMPLE 2

Preparation of 4-(methyl mercaptothiocarbonyl)-1,4-oxaza-spiro-(4,5)-decane Corresponding to the Formula (VI)

28.2 g (0.2 mole) of 1,4-oxaza-spiro-(4,5)-decane and 8.0 g (0.2 mole) of sodium hydroxide dissolved in 80 cm$^3$ of water was placed into a round-bottom flask equipped with a reflux condenser, a thermometer, a dropping funnel, and a stirrer. With continuous stirring and cooling, 15.2 g (12.05 cm$^3$, 0.2 mole) of carbon disulphide was added dropwise while the temperature was not allowed to rise above 20° C. As the introduction of carbon disulphide had been completed, the mixture was continued to stir at room temperature for 2 hours. Cooling was applied again with continuous stirring and 25.2 g (18.7 cm$^3$, 0.2 mole) of dimethyl sulphate was added dropwise below 10° C. Stirring was continued for 2 hours after the introduction had been completed. The aqueous layer was decanted then 20 cm$^3$ of water was added, stirred and decanted three times. The remained rubber-like crude product was boiled with four-fold amount of hexane. The cooled and filtrated product was a white powder uniform in thin-layer chromatography. Yield: 35.4 g (72.3%). Melting point after recrystallization from hexane: 79° to 81° C.

Elemental analysis: Theoretical: N=5.70, S=26.13. Measured: N=5.95, S=26.20.

EXAMPLE 3

Preparation of 3-(benzyl mercaptothiocarbonyl)-2-methyl-2-(tert.butyl)-oxazolidine Corresponding to the Formula (XXI)

28.6 g (0.2 mole) of 2-methyl-2-(tert.butyl)-oxazolidine and 8.0 g (0.2 mole) of sodium hydroxide dissolved in 80 cm$^3$ of water were placed into a round-bottom flask equipped with a reflux condenser, a thermometer, a dropping funnel and a stirrer. With continuous stirring and cooling, 15.2 g (12.05 cm$^3$, 0.2 mole) of carbon disulphide was introduced dropwise while the temperature was not allowed to rise above 20° C. As the introduction of carbon disulphide had been completed, the mixture was continued to stir at room temperature for 2 hours. Under cooling and stirring, 25.2 g (22.96 cm$^3$, 0.2 mole) of benzylchloride was added dropwise below 10° C. Stirring was continued for 2 hours after the introduction had been completed. The organic layer was separated from the aqueous one and the latter was extracted by chloroform. The unified organic phases were washed with water, dried above sodium sulphate, and then the solvent was distilled off. Yield: 36.8 g (61.8%).

Refractive index: $n_D^{22} = 1.5101$.

Elemental analysis: theoretical: N % = 4.53, S % = 20.72. measured: N % = 4.70, S % = 21.00.

General methods ro prepare the compounds of the formula (III) referred to in Table 1 are described as follows:

In a round bottom flask equipped with a stirrer, thermometer dropping funnel and a charging hole 0.1 mole of $R_9R_{10}$-amine and 0.1 mole of aqueous sodium hydroxide (10%) was introduced. With continuous stirring and ooling 0.1 mole of carbon disulphide was added and the temperature was not allowed to rise above 20° C. After 30 minute stirring the cooling was finished and the reaction mixture was stirred for 2 hours. During this time the formation of salt became complete. Then under constant cooling under 10° C. in small portins 0.075–0.08 mole of $R_{11}$-halogen compound was added. The mixture was stirred for 2 hours and was left standing until 24 hours. The proceeding of the reaction was followed by thin layer chromatography.

In case the reaction product is a suspension, then the solid product was filtrated, washed with water until it became neutral, then it was flushed with isopropyl alcohol and it was crystallized.

If the product is a rubber like product, then it is decanted, washed with water, then the rest was boiled with n-hexane and cooled while it was stirred. The precipitating solid product was decanted and if necessary purified as described above.

If the product is an oil, then it was extracted with a solvent like benzene or toluene from the alkaline aqueous sreaction mixture, then the organic phase was washed with water, aqueous sodium hydrogen carbonate, then again with water, dried over sodium sulphate and evaporated in vacuo (cf. Thorn, 6. D., Ludwig R. A. "The Dithiocarbamates and Related Compounds" Elsevier Publ. Co., Amsterdam-New York, 1962; Houben-Weyl: Methoden der organischen Chemie: Schwefel-, Selen-, Tellur-Verbindungen, Vol. 9. p 837–841/1955/).

| Compound Nr. | Mp. (°C.) $n_D^{22}$ | Elemental analysis N % theor. | found | S % theor. | found | Yield (%) |
|---|---|---|---|---|---|---|
| IV | 154–155 | 4,56 | 4,51 | 20,85 | 20,80 | 46,6 |
| V | 118–120 | 5,44 | 5,51 | 24,91 | 25,16 | 48,6 |
| VI | 79–81 | 5,70 | 5,95 | 26,13 | 26,20 | 72,3 |
| VII | 287 | 5,4 | 5,33 | 24,72 | 24,38 | 30,0 |
| VIII | 84–87 | | | 19,95 | 20,24 | 51,32 |
| IX | 120–122 | | | 19,11 | 19,10 | 47,69 |
| X | 136–141 | | | 17,94 | 17,35 | 50,12 |
| XI | 99–101 | | | 19,11 | 18,94 | 35,38 |
| XII | oil | | | 15,97 | 15,57 | 63,64 |
| XIII | 135–138 | | | 23,32 | 23,43 | 51,21 |
| XIV | 198–200 | | | 16,33 | 15,61 | 29,24 |
| XV | rubber | | | 14,23 | 13,87 | 79,52 |
| XVI | oil | | | 18,09 | 17,57 | 72,21 |

-continued

| Compound Nr. | Mp. (°C.) $n_D^{22}$ | Elemental analysis N % theor. | found | S % theor. | found | Yield (%) |
|---|---|---|---|---|---|---|
| XVII | 1,5931 | 4,68 | 4,42 | 21,41 | 20,9 | 56,0 |
| XVIII | 1,6861 | 4,62 | 4,42 | 21,13 | 20,30 | 42,6 |
| XIX | 115–116 | 4,63 | 4,72 | 21,20 | 19,95 | 47,6 |
| XX | 1,5353 | 4,25 | 4,00 | 19,46 | 19,20 | 40,2 |
| XXI | 1,5101 | 4,53 | 4,70 | 20,72 | 21,00 | 61,8 |
| XXII | oil | 4,98 | 4,80 | 22,78 | 22,10 | 46,5 |
| XXIII | oil | 5,24 | 5,04 | 23,98 | 23,20 | 44,8 |
| XXIV | oil | 4,98 | 4,70 | 22,77 | 22,3 | 45,2 |
| XXV | 75–76 | 5,53 | 5,60 | 25,31 | 24,45 | 85,9 |
| XXVI | 1,5898 | 5,23 | 5,25 | 23,97 | 23,75 | 74,9 |
| XXVII | 1,6142 | 5,32 | 5,25 | 24,34 | 24,20 | 88,8 |
| XXVIII | 1,6332 | 5,57 | 5,56 | 25,50 | 24,8 | 91,6 |
| XXIX | 1,6521 | 9,08 | 8,97 | 20,79 | 21,03 | 57,6 |
| XXX | 110 | 6,69 | 7,13 | 30,63 | 30,2 | 78,5 |

EXAMPLE 4

Preparation of a Concentrate 85 parts by weight of N,N-dipropylthiocarbamic acid S-ethyl ester (EPTC) was blended with 10 parts by weight of 4-(benzyl mercaptothiocarbonyl)-1,4-oxaza-spiro-(4,5)-decane (A) and with 5 parts by weight of oxyethylated anhydrosorbite monostearate (Tween 60). The concentrate produced contained 95 percent by weight of total active ingredients at a weight ratio of the herbicidal agent to the protecting agent of 8.5:1. The concentrate was easy to deliver and store. Before use, the concentrate should be diluted with an organic solvent such as xylene and with water to obtain a stable sprayable emulsion.

EXAMPLE 5

Preparation of an Emulsifiable Concentrate 50 parts by weight of N,N-dipropylthiocarbamic acid S-ethyl ester was blended with 10 parts by weight of 4-(allyl mercaptothiocarbonyl)-1,4-oxaza-spiro-(4,5)-decane and the blend was dissolved in 6 parts by weight of Tween 60 mixed with 46 parts by weight of xylene. The obtained emulsifiable concentrate was diluted with appropriate amount of water forming a stable emulsion sprayable to the area to be treated. The emulsifiable concentrate produced contained 60 percent of active ingredients at a ratio of the herbicidal agent to the protecting agent of 5:1.

EXAMPLE 6

Preparation of a Wettable Powder 10 parts by weight of N,N-diisobutyl thiocarbamic acid S-ethyl ester (butylate), 1 part by weight of 3-(benzyl-mercaptothiocarbonyl)-2-methyl-2-(tert.butyl)-oxazolidine, 1 part by weight of cetyl polyglycolether, and 88 parts by weight of caolin were blended then ground in a ball mill. The wettable powder obtained contained 11 percent of active ingredients at a weight ratio of the herbidical agent to the protecting agent of 10:1.

EXAMPLE 7

Preparation of Granules 10 parts by weight of 4-(methyl mercaptothiocarbonyl)-1,4-oxaza-spiro-(4,5)-decane was blended with 2.5 parts by weight of epichlorohydrine. The blend was dissolved in 70 parts by weight of acetone then 2.5 parts by weight of cetyl polyglycolether and 25 parts by weight of poly(ethylene glycol) were added to the solution. The solution was sprayed onto 950 parts by weight of caolin (particle size: 0.5 to 0.9 mm) then acetone was evaporated in vacuo. The granulated product contained 1 percent by weight of antidote.

Following a procedure analogous with the precedent examples, appropriate compositions can be prepared using an antidote corresponding to the formula (III) and a herbicide corresponding to the formula (I) or (II). Compositions containing only the antidote, together with suitable additives, may also be prepared.

BIOLOGICAL EXAMPLES

The protecting activity of the antidote of this invention was tested in a greenhouse when used along with thiolcarbamate herbicides.

EXAMPLE 8

Culture-trays of 30×40×19 cm were filled with quartz sand to a layer thickness of 10 cm. 100 seeds of maize (BEMA 210 TC hybrid) were sowed in each tray. The sand was sprayed with 0.228 g (10 kg/hectare) of a herbicidal thiolcarbamate derivative and 0.0228 g (1 kg/hectare) of protecting agent or the emulsifiable concentrate of the same amount of protecting agent diluted with 1 dm³/hectare of water. After spraying, another 2 cm of sand layer was spread over the treated surface. Culture-trays were watered daily and phytotoxic lesions were evaluated in every 5 days, finally after 4 weeks (Table 2).

Selectivity of the composition to maize was defined as a percentage of injuries in the presence of the protecting agent(s) on a scale where the percentage of lesions was regarded 0 and 100 in the untreated control and in the cultures treated with the herbicide only, respectively.

It can be seen that 4-(benzyl mercaptothiocarbonyl)-1,4-oxaza-spiro-(4,5)-decane (IV) was more efficient in enhancing the selectivity of EPTC than the commercial antidote R-25,788.

In small-plot field experiments (5×2.5 m = 12.5 m² in four series each), before sowing maize, the soil was sprayed with 10 kg/hectare of N,N-dipropyl thiocarbamic acid S-ethyl ester (EPTC) hervicidal agent and the aqueous emulsion of the emulsifiable concentrate prepared according to Example 5 containing a protecting agent composition of this invention. The chemicals were ploughed into the soil by a rotation cultivator to a depth of about 4 to 6 cm. Then Maize was sowed. Between the rows of maize, seeds of the following monocotyledonous and dicotyledonous weeds, 5 g each, were sowed: millet (*Panicum miliaceum*) and foxtail (*setaria viridis*). Four series of experiments were installed. EPTAM 6E containing 72 percent of EPTC as active ingredient was used as standard (Table 3).

Selectivity of the composition to maize was defined as a percentage of lesions in the presence of the protecting agent(s) on a scale where the percentage of lesions was regarded 0 and 100 in the untreated control and in cultures treated with the herbicide only, respectively.

It can be seen in Tables 2 and 3 that a combined application of EPTC + antidote according to this invention was advantageous since its protecting efficiency was higher than that of the known antidotes while maintaining the high weed-killing activity. It can also be seen that the herbicidal efficiency of the favourable thiolcarbamate was not influenced appreciably by the presence of antidotes.

TABLE 2

| Treatment | Dose of agents (kg/ha) | Sprouted plants (pc.) | Teratoid plants (%) | Killed (%) | Height at age of 3 weeks (cm) | Green weight of 90 plants (g) | Selectivity (%) |
|---|---|---|---|---|---|---|---|
| CONTROL | 0 | 98 | 0 | 0 | 38 | 210 | 100 |
| A | 10 | 90 | 80 | 90 | 32 | 211 | 0 |
| A + B standard | 10 + 1 | 96 | 0 | 0 | 34 | 216 | 90 |
| A + C | 10 + 1 | 96 | 0 | 0 | 35 | 218 | 100 |
| A + D | 10 + 1 | 97 | 5 | 10 | 29 | 211 | 80 |
| A + E | 10 + 1 | 95 | 20 | 35 | 24 | 211 | 60 |

A: N,N-dipropyl thiocarbamic acid S-ethyl ester (EPTC)
B: N,N-diallyl dichloroacetamide (R-25,788, commercial)
C: antidote IV
D: antidote V
E: antidote XXI

TABLE 3

| Treatment | Dose of agents (kg/ha) | Teratoid plants (pc.) | Selectivity (%) | Herbicidal activity (%) PANMI | Herbicidal activity (%) SETVI |
|---|---|---|---|---|---|
| CONTROL | 0 | 0 | 100 | 0 | 0 |
| A | 10 | 15 | 0 | 100 | 100 |
| A + B | 10 + 1 | 2 | 95 | 100 | 100 |
| A + C | 10 + 1 | 0 | 100 | 100 | 100 |
| A + D | 10 + 1 | 6 | 80 | 100 | 100 |
| A + E | 10 + 1 | 9 | 60 | 100 | 100 |

A: N,N-dipropyl thiocarbamic acid S-ethyl ester (EPTC)
B: N,N-diallyl dichloroacetamide (R-25-788)
C: antidote IV
D: antidote V
E: antidote XXI
Abbreviations:
PANMI = *Panicum miliaceum*
SETVI = *Setaria viridis*

EXAMPLE 9

Culture-trays of 30×40×19 cm were filled with quartz sand to a layer thickness of 10 cm. 100 seeds of maize (BEMA 210 TC hybrid) were sowed into each tray. The sand was sprayed with 0.228 g (10 kg/hectare) of a herbicidal thiolcarbamate derivative and 0.0228 g (1 kg/hectare) of protecting agent or the emulsifiable concentrate of the same amount of protecting agent diluted with 1 dm³/hectare of water. After spraying, another 2 cm of sand layer was spread over the treated surface. Culture-trays were watered daily and phytotoxic lesions were evaluated in every 5 days, finally after 4 weeks (Table 4).

TABLE 4

Maize hybride BEMA 210 TC

| | | Out of 100 seeds of maize | | | | | |
|---|---|---|---|---|---|---|---|
| Treatment | Dose of agents (kg/ha) | Sprouted plants (pc.) | Treatoid plants (%) | Killed (%) | Height at age of 4 weeks (cm) | Green weight of 92 plants (g) | Selectivity (%) |
| CONTROL | 0 | 98 | 0 | 0 | 40 | 235 | 100 |
| A | 10 | 94 | 40 | 40 | 34 | 210 | 40 |
| A + B standard | 10 + 1 | 97 | 4 | 4 | 36 | 216 | 90 |
| A + C | 10 + 1 | 98 | 2 | 2 | 37 | 210 | 95 |
| A + D | 10 + 1 | 97 | 2 | 2 | 21 | 205 | 90 |
| A + E | 10 + 1 | 95 | 3 | 3 | 26 | 205 | 90 |

A: N,N-diisobutyl thiocarbamic acid S-ethyl ester (butylate)
B: N,N-diallyl dichloroacetamide (R-25.788, commercial)
C: antidote (IV)
D: antidote (V)
E: antidote (XXI)

EXAMPLE 10

Culture-trays of 30×40×19 cm were filled with a 1:1 mixture of quartz sand and brown forest-soil to a layer thickness of 12 cm. 100 seeds of maize were sowed in each tray. As a pre-emergent treatment, 0.5 cm$^3$ (5 dm$^3$/hectare) of herbicidal chloroacetanilide and 0.05 g (0.5 kg/hectare) of protecting agent were applied. Culture-trays were watered daily and phytotoxic lesions were evaluated in every 5 days, finally after 4 weeks cultures treated with the herbicide only, respectively (Table 6).

In Table 6, a prominent advantage of combined application of acetochlor + antidote according to this invention is demonstrated: they provided more efficient protection than the known antidotes while maintaining the high herbicidal activity.

It can be seen that the favourable herbicidal effect of chloroacetanilide was not influenced by the presence of antidotes.

TABLE 5

| | | Out of 100 seeds of maize | | | | | |
|---|---|---|---|---|---|---|---|
| Treatment | Dose of agents (kg/ha) | Sprouted plants (pc.) | Teratoid plants (%) | Killed (%) | Height at age of 2 weeks (cm) | Green weight of 85 plants (g) | Selectivity (%) |
| CONTROL | 0 | 97 | 0 | 0 | 26 | 240 | 100 |
| A | 5 | 86 | 81 | 88 | 4.5 | 62 | 0 |
| A + B standard | 5 + 0.5 | 96 | 2 | 1 | 19.5 | 119 | 90 |
| A + C | 5 + 0.5 | 96 | 0 | 0 | 23 | 124 | 100 |
| A + D | 5 + 0.5 | 94 | 14 | 2 | 20 | 112 | 85 |
| A + E | 5 + 0.5 | 95 | 10 | 1 | 20 | 119 | 89 |

A: 2-chloro-N-(ethoxymethyl)-N-(2'-ethyl-6'-methyl-phenyl)-acetmide (acetochlor)
B: N,N-diallyl dichloroacetamide (R-25.788)
C: antidote (IV)
D: antidote (V)
E: N-dichloroacetyl-oxa-4-azaspiro-(4,5)-decane (AD-67) commercial (Table 5).

Selectivity of the composition to maize was defined as a percentage of lesions in the presence of the protecting agent(s) on a scale where the percentage of lesions was regarded 0 and 100 in the untreated control and in the cultures treated with the herbicide only, respectively.

It can be seen that 4-(benzyl mercaptothiocarbonyl)-1,4-oxaza-spiro-(4,5)-decane (IV) was more efficient antidote than the commercial antidote, R-25.788, in enhancing the selectivity of acetochlor.

In small-plot field experiments (5×2.5 m = 12.5 m$^2$ in four series each), after sowing maize (pre-emergent treatment), the soil was sprayed with 5 cm$^3$/hectare of 2-chloro-N-(ethoxymethyl)-N-(2-ethyl-6-methyl-phenyl)-acetamide (acetochlor) herbicidal agent. Predominant weeds on the experimental plots were *Echinochloa crus galli* and *Setaria viridis*.

Selectivity of the composition to maize was defined as a percentage of lesions in the presence of the protecting agent(s) on a scale where the percentage of lesions was regarded 0 and 100 in the untreated control and in

TABLE 6

| Treatment | Dose of agents (kg/ha) | Teratoid plants (pc.) | Selectivity (%) | Herbicidal activity (%) | |
|---|---|---|---|---|---|
| | | | | ECHCR | SETVI |
| CONTROL | 0 | 0 | 100 | 0 | 0 |
| A | 5 | 18 | 0 | 100 | 100 |
| A + B standard | 5 + 0.5 | 3 | 95 | 100 | 100 |
| A + C | 5 + 0.5 | 0 | 100 | 100 | 100 |
| A + D | 5 + 0.5 | 7 | 80 | 100 | 100 |

A: 2-chloro-N-(ethoxymethyl)-N-(2'-ethyl-6'-methyl-phenyl)-acetamide (acetochlor)
B: N-dichloroacetyl-oxa-4-azospiro-(4,5)-decane (AD-67)
C: antidote (IV)
D: antidote (V)

In the followings, the internationally accepted EWRC rating was used for the comparison of the detrimental effect of compositions and combinations of this invention on the maize plant and on weeds to the untreated control.

EWRC rating is interpreted as follows:

| Herbicidal activity (%) | General impressions | EWRC rating | Phytotoxic symptoms on cultivated plants |
|---|---|---|---|
| 100 | excellent | 1 | No symptom |
| 98 | very good | 2 | very slight symptoms |
| 95 | good | 3 | slight symptoms |
| 90 | satisfactory | 4 | strong but possibly transient symptoms reduced yield is improbable |
| 82 | doubtful | 5 | symptoms of unknown consequences |
| 70 | unsatisfactory | 6 | perceptible detrimental symptoms |
| 55 | bad | 7 | strong detrimental symptoms |
| 30 | very bad | 8 | very strong detrimental symptoms |
| 0 | useless | 9 | complete extermination |

EXAMPLE 11

The efficiency in the protecting activity of the compositions of this invention against herbicides is illustrated in Table 7. The experiments were conducted in a greenhouse using maize (Sabrina) planted into culture-trays. 1:1 mixture of brown forest-soil and sand was used. Pre-emergent or pre-sowing treatments were applied.

TABLE 7

| Ser. No. | Herbicide and antidote | Dose g/ha | Phytotoxicity on maize EWRC rating |
|---|---|---|---|
| 1. | Acetochlor | 1000 | 7 |
| 2. | Acetochlor + AD-67 | 1000 + 200 | 2 |
| 3. | Acetochlor + MG-191 | 1000 + 200 | 1 |
| 4. | Acetochlor + IV. | 1000 + 200 | 2 |
| 5. | Acetochlor + V. | 1000 + 200 | 1 |
| 6. | Acetochlor + VI. | 1000 + 200 | 2 |
| 7. | Acetochlor + VII. | 1000 + 200 | 3 |
| 8. | Acetochlor + VIII. | 1000 + 200 | 1 |
| 9. | Acetochlor + IX. | 1000 + 200 | 2 |
| 10. | Acetochlor + X. | 1000 + 200 | 3 |
| 11. | Acetochlor + XI. | 1000 + 200 | 2 |
| 12. | Acetochlor + XII. | 1000 + 200 | 3 |
| 13. | Acetochlor + XIII. | 1000 + 200 | 1 |
| 14. | Acetochlor + XIV. | 1000 + 200 | 2 |
| 15. | Acetochlor + XV. | 1000 + 200 | 4 |
| 16. | Acetochlor + XVI. | 1000 + 200 | 3 |
| 17. | Acetochlor + XVII. | 1000 + 200 | 3 |
| 18. | Acetochlor + XVIII. | 1000 + 200 | 3 |
| 19. | Acetochlor + XIX. | 1000 + 200 | 2 |
| 20. | Acetochlor + XX. | 1000 + 200 | 2 |
| 21. | Acetochlor + XXI. | 1000 + 200 | 3 |
| 22. | Acetochlor + XXII. | 1000 + 200 | 3 |
| 23. | Acetochlor + XXIII. | 1000 + 200 | 2 |
| 24. | Acetochlor + XXIV. | 1000 + 200 | 3 |
| 25. | Acetochlor + XXV. | 1000 + 200 | 2 |
| 26. | Acetochlor + XXVI. | 1000 + 200 | 3 |
| 27. | Acetochlor + XXVII | 1000 + 200 | 3 |
| 28. | Acetochlor + XXVIII. | 1000 + 200 | 3 |
| 29. | Acetochlor + XXIX. | 1000 + 200 | 2 |
| 30. | Acetochlor + XXX. | 1000 + 200 | 2 |
| 31. | Alachlor | 1500 | 7 |
| 32. | Alachlor + AD-67 | 1500 + 200 | 2 |
| 33. | Alachlor + IV. | 1500 + 200 | 1 |
| 34. | Alachlor + V. | 1500 + 200 | 1 |
| 35. | Alachlor + VIII. | 1500 + 200 | 2 |
| 36. | Alachlor + IX. | 1500 + 200 | 2 |
| 37. | Alachlor + XIII. | 1500 + 200 | 1 |
| 38. | Alachlor + XIX. | 1500 + 200 | 2 |
| 39. | Propachlor | 2000 | 4 |
| 40. | Propachlor + AD-67 | 2000 + 200 | 1 |
| 41. | Propachlor + IV. | 2000 + 200 | 1 |
| 42. | Propachlor + V. | 2000 + 200 | 1 |
| 43. | Metolachlor | 1500 | 6 |
| 44. | Metolachlor + AD-67 | 1500 + 200 | 3 |
| 45. | Metolachlor + IV. | 1500 + 200 | 1 |
| 46. | Metolachlor + V. | 1500 + 200 | 2 |
| 47. | Metolachlor + VIII. | 1500 + 200 | 2 |
| 48. | Metolachlor + IX. | 1500 + 200 | 3 |
| 49. | Metolachlor + XI. | 1500 + 200 | 3 |
| 50. | Metolachlor + XIII. | 1500 + 200 | 1 |
| 51. | Metolachlor + XIX. | 1500 + 200 | 3 |
| 52. | EPTC | 2000 | 7 |
| 53. | EPTC + AD-67 | 2000 + 200 | 2 |
| 54. | EPTC + MG-191 | 2000 + 200 | 1 |
| 55. | EPTC + IV. | 2000 + 200 | 2 |
| 56. | EPTC + V. | 2000 + 200 | 1 |
| 57. | EPTC + VI. | 2000 + 200 | 2 |
| 58. | EPTC + VII. | 2000 + 200 | 4 |
| 59. | EPTC + VIII. | 2000 + 200 | 1 |

TABLE 7-continued

| Ser. No. | Herbicide and antidote | Dose g/ha | Phytotoxicity on maize EWRC rating |
|---|---|---|---|
| 60. | EPTC + IX. | 2000 + 200 | 2 |
| 61. | EPTC + X. | 2000 + 200 | 2 |
| 62. | EPTC + XI. | 2000 + 200 | 1 |
| 63. | EPTC + XII. | 2000 + 200 | 4 |
| 64. | EPTC + XIII. | 2000 + 200 | 1 |
| 65. | EPTC + XIV. | 2000 + 200 | 3 |
| 66. | EPTC + XV. | 2000 + 200 | 4 |
| 67. | EPTC + XVI. | 2000 + 200 | 4 |
| 68. | EPTC + XVII. | 2000 + 200 | 3 |
| 69. | EPTC + XVIII. | 2000 + 200 | 2 |
| 70. | EPTC + XIX. | 2000 + 200 | 3 |
| 71. | EPTC + XX. | 2000 + 200 | 2 |
| 72. | EPTC + XXI. | 2000 + 200 | 3 |
| 73. | EPTC + XXII. | 2000 + 200 | 3 |
| 74. | EPTC + XXIII. | 2000 + 200 | 2 |
| 75. | EPTC + XXIV. | 2000 + 200 | 2 |
| 76. | EPTC + XXV. | 2000 + 200 | 3 |
| 77. | EPTC + XXVI. | 2000 + 200 | 4 |
| 78. | EPTC + XXVII. | 2000 + 200 | 3 |
| 79. | EPTC + XXVIII. | 2000 + 200 | 2 |
| 80. | EPTC + XXIX. | 2000 + 200 | 2 |
| 81. | EPTC + XXX. | 2000 + 200 | 1 |
| 82. | butylate | 2500 | 6 |
| 83. | butylate + AD-67 | 2500 + 200 | 2 |
| 84. | butylate + IV. | 2500 + 200 | 2 |
| 85. | butylate + V. | 2500 + 200 | 1 |
| 86. | butylate + VIII. | 2500 + 200 | 1 |
| 87. | butylate + IX. | 2500 + 200 | 2 |
| 88. | butylate + XI. | 2500 + 200 | 3 |
| 89. | butylate + XIII. | 2500 + 200 | 2 |
| 90. | butylate + XIX. | 2500 + 200 | 2 |
| 91. | Acetochlor + EPTC | 1000 + 1800 | 7-8 |
| 92. | Acetochlor + EPTC + AD-67 | 1000 + 1800 + 450 | 3 |
| 93. | Acetochlor + EPTC + MG-191 | 1000 + 1800 + 450 | 2 |
| 94. | Acetochlor + EPTC + IV. | 1000 + 1800 + 450 | 3 |
| 95. | Acetochlor + EPTC + V. | 1000 + 1800 + 450 | 2 |
| 96. | Acetochlor + EPTC + VI. | 1000 + 1800 + 450 | 2 |
| 97. | Acetochlor + EPTC + VII. | 1000 + 1800 + 450 | 5 |
| 98. | Acetochlor + EPTC + VIII. | 1000 + 1800 + 450 | 2 |
| 99. | Acetochlor + EPTC + IX. | 1000 + 1800 + 450 | 3 |
| 100. | Acetochlor + EPTC + X. | 1000 + 1800 + 450 | 3 |
| 101. | Acetochlor + EPTC + XI. | 1000 + 1800 + 450 | 3 |
| 102. | Acetochlor + EPTC + XII. | 1000 + 1800 + 450 | 4 |
| 103. | Acetochlor + EPTC + XIII. | 1000 + 1800 + 450 | 2 |
| 104. | Acetochlor + EPTC + XIV. | 1000 + 1800 + 450 | 3 |
| 105. | Acetochlor + EPTC + XV. | 1000 + 1800 + 450 | 3 |
| 106. | Acetochlor + EPTC + XVI. | 1000 + 1800 + 450 | 4 |
| 107. | Acetochlor + EPTC + XVII. | 1000 + 1800 + 450 | 4 |
| 108. | Acetochlor + EPTC + XVIII. | 1000 + 1800 + 450 | 3 |
| 109. | Acetochlor + EPTC + XIX. | 1000 + 1800 + 450 | 3 |
| 110. | Acetochlor + EPTC + XX. | 1000 + 1800 + 450 | 3 |
| 111. | Acetochlor + EPTC + XXI. | 1000 + 1800 + 450 | 4 |
| 112. | Acetochlor + EPTC + XXII. | 1000 + 1800 + 450 | 3 |
| 113. | Acetochlor + EPTC + XXIII. | 1000 + 1800 + 450 | 2 |
| 114. | Acetochlor + EPTC + XXIV. | 1000 + 1800 + 450 | 3 |
| 115. | Acetochlor + EPTC + XXV. | 1000 + 1800 + 450 | 4 |
| 116. | Acetochlor + EPTC + XXVI. | 1000 + 1800 + 450 | 4 |
| 117. | Acetochlor + EPTC + XXVII. | 1000 + 1800 + 450 | 4 |
| 118. | Acetochlor + EPTC + XXVIII. | 1000 + 1800 + 450 | 3 |
| 119. | Acetochlor + EPTC + XXIX. | 1000 + 1800 + 450 | 4 |
| 120. | Acetochlor + EPTC + XXX. | 1000 + 1800 + 450 | 2 |

Low-organic solid deficient in inorganic colloids highly predispose to the development of phytotoxic effects. Experiments conducted on such a soil revealed inevitably that antidote-less compositions deteriorate maize strongly. Phytotoxicities were given by averaging 4 repeated results. From the EWRC ratings it can be seen that each of the examined antidotes appropriately protected the maize from the deteriorating effect of the applied herbicides (EWRC 4 rating=strong but possibly transient symptoms, reduced yield is improbable).

EXAMPLE 12

In order to determine the effective amount of the antidotes of this invention per hectare, the herbicidal activities and EWRC ratings for the lesion of maize were determined in a field experiment with pre-sowing treatments. The optimum amounts of herbicides and antidotes are presented in Table 8.

TABLE 8

| Ser. No. | Herbicide and antidote applied | Dose (g/ha) | Reading | Herbicidal activity (EWRC) SEIGL | ECHCR | AMARE | CHEAL | Phytotoxicity on maize (EWRC) |
|---|---|---|---|---|---|---|---|---|
| 1. | Acetochlor + AD-67 | 2000 + 400 | (1) | 1 | 2 | 3 | 4 | 2 |
| | | | (2) | 2 | 2 | 4 | 4 | 1 |
| 2. | Acetochlor + VIII. | 2000 + 400 | (1) | 1 | 1 | 3 | 3 | 2 |
| | | | (2) | 2 | 2 | 4 | 5 | 2 |
| 3. | Acetochlor + XIII. | 2000 + 400 | (1) | 1 | 1 | 3 | 3 | 1 |
| | | | (2) | 2 | 2 | 4 | 4 | 1 |
| 4. | Acetochlor + XX. | 2000 + 400 | (1) | 1 | 1 | 3 | 4 | 2 |
| | | | (2) | 2 | 2 | 4 | 5 | 1 |
| 5. | Acetochlor + XXII. | 2000 + 400 | (1) | 1 | 1 | 4 | 4 | 2 |
| | | | (2) | 1 | 2 | 4 | 5 | 1 |
| 6. | Acetochlor + XXIII. | 2000 + 400 | (1) | 1 | 1 | 3 | 4 | 1 |
| | | | (2) | 1 | 2 | 4 | 4 | 1 |
| 7. | Acetochlor + AD-67 | 4000 + 800 | (1) | 1 | 1 | 2 | 2 | 4 |
| | | | (2) | 1 | 2 | 3 | 4 | 3 |
| 8. | Acetochlor + VIII. | 4000 + 800 | (1) | 1 | 1 | 2 | 3 | 4 |
| | | | (2) | 1 | 1 | 3 | 3 | 3 |
| 9. | Acetochlor + XIII. | 4000 + 800 | (1) | 1 | 1 | 2 | 2 | 2 |
| | | | (2) | 1 | 2 | 3 | 3 | 1 |
| 10. | Acetochlor + XX. | 4000 + 800 | (1) | 1 | 1 | 2 | 3 | 5 |
| | | | (2) | 1 | 1 | 3 | 4 | 3 |
| 11. | Acetochlor + XXII. | 4000 + 800 | (1) | 1 | 1 | 2 | 2 | 5 |
| | | | (2) | 1 | 1 | 3 | 4 | 4 |
| 12. | Acetochlor + XXIII. | 4000 + 800 | (1) | 1 | 1 | 2 | 3 | 4 |
| | | | (2) | 1 | 1 | 3 | 3 | 2 |
| 13. | EPTC + AD-67 | 3500 + 450 | (1) | 1 | 2 | 4 | 5 | 1 |
| | | | (2) | 2 | 2 | 5 | 6 | 1 |
| 14. | EPTC + VIII. | 3500 + 450 | (1) | 1 | 1 | 4 | 4 | 2 |
| | | | (2) | 1 | 2 | 5 | 5 | 1 |
| 15. | EPTC + XIII. | 3500 + 450 | (1) | 1 | 2 | 4 | 5 | 1 |
| | | | (2) | 1 | 2 | 5 | 5 | 1 |
| 16. | EPTC + XX. | 3500 + 450 | (1) | 1 | 2 | 3 | 4 | 2 |
| | | | (2) | 2 | 2 | 4 | 4 | 1 |
| 17. | EPTC + XXII. | 3500 + 450 | (1) | 1 | 1 | 3 | 4 | 1 |
| | | | (2) | 2 | 2 | 4 | 5 | 1 |
| 18. | EPTC + XXIII. | 3500 + 450 | (1) | 1 | 2 | 3 | 4 | 1 |
| | | | (2) | 1 | 2 | 4 | 4 | 1 |
| 19. | EPTC + AD-67 | 7000 + 900 | (1) | 1 | 1 | 3 | 4 | 3 |
| | | | (2) | 1 | 2 | 4 | 5 | 2 |
| 20. | EPTC + VIII. | 7000 + 900 | (1) | 1 | 2 | 4 | 5 | 2 |
| | | | (2) | 1 | 2 | 4 | 5 | 1 |
| 21. | EPTC + XIII. | 7000 + 900 | (1) | 1 | 1 | 4 | 4 | 2 |
| | | | (2) | 1 | 2 | 4 | 5 | 1 |
| 22. | EPTC + XX. | 7000 + 900 | (1) | 1 | 1 | 2 | 3 | 4 |
| | | | (2) | 1 | 1 | 3 | 4 | 3 |
| 23 | EPTC + XXII. | 7000 + 900 | (1) | 1 | 1 | 4 | 3 | 3 |
| | | | (2) | 1 | 1 | 4 | 4 | 3 |
| 24. | EPTC + XXIII. | 7000 + 900 | (1) | 1 | 1 | 3 | 4 | 3 |
| | | | (2) | 1 | 1 | 4 | 4 | 2 |
| 25. | Acetochlor + EPTC + AD-67 | 1000 + 1800 + 450 | (1) | 2 | 3 | 4 | 4 | 1 |
| | | | (2) | 4 | 4 | 4 | 5 | 1 |
| 26. | Acetochlor + EPTC + IV. | 1000 + 1800 + 450 | (1) | 2 | 2 | 4 | 4 | 1 |
| | | | (2) | 4 | 4 | 5 | 5 | 1 |
| 27. | Acetochlor + EPTC + V. | 1000 + 1800 + 450 | (1) | 2 | 3 | 4 | 4 | 1 |
| | | | (2) | 4 | 4 | 5 | 6 | 1 |
| 28. | Acetochlor + EPTC + AD-67 | 2000 + 3600 + 900 | (1) | 1 | 1 | 1 | 2 | 2 |
| | | | (2) | 1 | 1 | 2 | 3 | 1 |
| 29. | Acetochlor + EPTC + IV. | 2000 + 3600 + 900 | (1) | 1 | 1 | 1 | 2 | 1 |
| | | | (2) | 1 | 1 | 2 | 2 | 1 |
| 30. | Acetochlor + EPTC + V. | 2000 + 3600 + 900 | (1) | 1 | 1 | 1 | 2 | 1 |
| | | | (2) | 1 | 1 | 2 | 2 | 1 |
| 31. | Acetochlor + EPTC + VIII. | 2000 + 3600 + 900 | (1) | 1 | 1 | 1 | 2 | 2 |
| | | | (2) | 1 | 1 | 1 | 3 | 2 |
| 32. | Acetochlor + EPTC + XIII. | 2000 + 3600 + 900 | (1) | 1 | 1 | 1 | 2 | 1 |
| | | | (2) | 1 | 1 | 2 | 2 | 1 |
| 33. | Acetochlor + EPTC + XX. | 2000 + 3600 + 900 | (1) | 1 | 1 | 2 | 2 | 4 |
| | | | (2) | 1 | 1 | 2 | 3 | 3 |
| 34. | Acetochlor + EPTC + XXII. | 2000 + 3600 + 900 | (1) | 1 | 1 | 2 | 2 | 3 |
| | | | (2) | 1 | 1 | 3 | 3 | 3 |
| 35. | Acetochlor + EPTC + XXIII. | 2000 + 3600 + 900 | (1) | 1 | 1 | 2 | 2 | 3 |
| | | | (2) | 1 | 1 | 2 | 3 | 2 |
| 36. | Acetochlor + EPTC + AD-67 | 4000 + 7200 + 1350 | (1) | 1 | 1 | 1 | 1 | 6 |
| | | | (2) | 1 | 1 | 1 | 2 | 4 |
| 37. | Acetochlor + EPTC + IV. | 4000 + 7200 + 1350 | (1) | 1 | 1 | 1 | 1 | 4 |
| | | | (2) | 1 | 1 | 1 | 2 | 4 |
| 38. | Acetochlor + EPTC + V. | 4000 + 7200 + 1350 | (1) | 1 | 1 | 1 | 1 | 5 |
| | | | (5) | 1 | 1 | 1 | 2 | 4 |
| 39. | Acetochlor + EPTC + VIII. | 4000 + 7200 + 1350 | (1) | 1 | 1 | 1 | 1 | 5 |
| | | | (2) | 1 | 1 | 1 | 2 | 4 |
| 40. | Acetochlor + EPTC + | 4000 + 7200 + | (1) | 1 | 1 | 1 | 1 | 4 |

TABLE 8-continued

| Ser. No. | Herbicide and antidote applied | Dose (g/ha) | Reading | Herbicidal activity (EWRC) SEIGL | ECHCR | AMARE | CHEAL | Phytotoxicity on maize (EWRC) |
|---|---|---|---|---|---|---|---|---|
|  | XIII. | 1350 | (2) | 1 | 1 | 1 | 1 | 3 |
| 41. | Acetochlor + EPTC + XX. | 4000 + 7200 + 1350 | (1) (2) | 1 1 | 1 1 | 1 2 | 1 2 | 5 4 |
| 42. | Acetochlor + EPTC + XXII. | 4000 + 7200 + 1350 | (1) (2) | 1 1 | 1 1 | 1 2 | 2 2 | 5 4 |
| 43. | Acetochlor + EPTC + XXIII. | 4000 + 7200 + 1350 | (1) (2) | 1 1 | 1 1 | 1 2 | 1 2 | 4 3 |
| 44. | Alachlor + EPTC + V. | 2400 + 3600 + 900 | (1) (2) | 1 1 | 1 2 | 2 3 | 2 3 | 2 2 |
| 45. | Alachlor + EPTC + IV. | 2400 + 3600 + 900 | (1) (2) | 1 1 | 1 2 | 2 2 | 2 2 | 1 1 |
| 46. | Alachlor + EPTC + V. | 4800 + 7200 + 1800 | (1) (2) | 1 1 | 1 1 | 1 2 | 2 3 | 4 3 |
| 47. | Alachlor + EPTC + IV. | 4800 + 7200 + 1800 | (1) (2) | 1 1 | 1 1 | 1 2 | 2 2 | 3 2 |
| 48. | Acetochlor + Butylate V. | 2000 + 4000 + 900 | (1) (2) | 1 1 | 1 1 | 2 2 | 2 3 | 2 1 |
| 49. | Acetochlor + butylate + IV. | 2000 + 4000 + 900 | (1) (2) | 1 1 | 1 1 | 2 2 | 2 2 | 1 1 |
| 50. | Acetochlor + butylate + V. | 4000 + 8000 + 1800 | (1) (2) | 1 1 | 1 1 | 1 1 | 2 2 | 5 4 |
| 51. | Acetochlor + butylate + IV. | 4000 + 8000 + 1800 | (1) (2) | 1 1 | 1 1 | 1 1 | 2 2 | 5 5 |
| 52. | Alachlor + butylate + V. | 2400 + 4000 + 900 | (1) (2) | 1 1 | 2 2 | 3 4 | 3 4 | 1 1 |
| 53. | Alachlor + Butylate + IV IV | 2400 + 4000 + 900 | (1) (2) | 1 1 | 2 2 | 3 4 | 4 4 | 2 1 |
| 54. | Alachlor + butylate + V | 4800 + 8000 + 1800 | (1) (2) | 1 1 | 1 1 | 2 3 | 2 2 | 2 1 |
| 55. | Alachlor + butylate + IV | 4800 + 8000 + 1800 | (1) (2) | 1 1 | 1 1 | 2 3 | 2 3 | 2 1 |

SETLG = Setaria glanca
ECHCR = Echinochloa crus-galli
AMARE = Amaranthus retroflexus
CHEAL = Chenopodium album The experiments were read (1) on May 27 and (2) on August 18. Antidotes of this invention were highly safe in protecting maize against the combinations in Table 8 even though these herbicides themselves might be toxic to maize. The most active representatives of the herbicide group consisting of chloroacetanilide and thiolcarbamate were selected to these experiments which have the lowest selectivity on maize.

We claim:

1. A herbicide composition comprising a herbicidally effective amount of a thiolcarbamate derivative of the formula

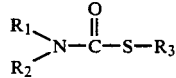

(I)

wherein $R_1$, $R_2$, and $R_3$ are independently of one another $C_{1-4}$ alkyl, or $R_1$ or $R_2$ is a $C_{4-6}$ cycloalkyl group and as a safener (antidote) an antidotally effective amount of a dithiocarbamic acid derivative of the formula

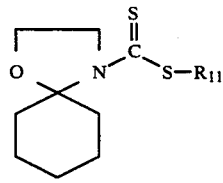

(III)

wherein $R_{11}$ is a $C_{1-3}$ alkyl or $C_{2-3}$ alkenyl group, the weight ratio of the herbicide of formula (I) to the safener of formula (III) being from 50:1 to 5:1.

2. A composition according to claim 1, further comprising a solid or liquid carrier and a surfactant.

3. A composition according to claims 1 or 2, wherein a compound of formula (III) is present at a concentration of from 1% to 90% by weight.

4. A composition according to claim 1, further comprising a herbicidally effective amount of a chloroacetanilide of the formula

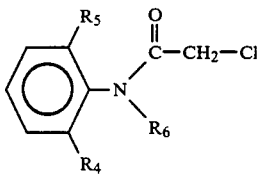

(II)

wherein
$R_4$ and $R_5$ are independently from one another hydrogen or a $C_{1-4}$ alkyl group,
$R_6$ is an alkoxyalkyl moiety of the formula

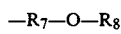

wherein $R_7$ and $R_8$ are independently of one another a $C_{1-4}$ alkyl group.

5. A method of selective weed control comprising treating the soil prior to or after sowing with a composition of claim 1.

6. Method of seed dressing which comprises treating a seed of a plant to be cultivated by a dithiocarbamic acid derivative of formula (III) of claim 1.
7. A compound of the formula
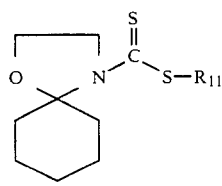
wherein $R_{11}$ is a $C_{1-3}$ alkyl or $C_{2-3}$ alkenyl group.
* * * * *